United States Patent [19]
Lippsmeier et al.

[11] 3,998,886
[45] * Dec. 21, 1976

[54] PRODUCTION OF HALOGEN-CONTAINING TERTIARY PHOSPHINE OXIDES

[75] Inventors: Bernd Lippsmeier, Hurth-Knapsack; Klaus Hestermann, Erftstadt Bliesheim; Hubert Neumaier, Hurth-Knapsack, all of Germany

[73] Assignee: Hoechst Aktiengesellschaft, Frankfurt am Main, Germany

[ * ] Notice: The portion of the term of this patent subsequent to Dec. 14, 1993, has been disclaimed.

[22] Filed: Mar. 13, 1975

[21] Appl. No.: 557,926

[30] Foreign Application Priority Data

Mar. 16, 1974 Germany .......................... 2412800

[52] U.S. Cl. ..................................... 260/606.5 P
[51] Int. Cl.$^2$ ..................................... C07F 9/02
[58] Field of Search ............................ 260/606.5 P

[56] References Cited

UNITED STATES PATENTS

| | | | |
|---|---|---|---|
| 3,716,580 | 2/1973 | Maier | 260/606.5 P |
| 3,732,316 | 5/1973 | Lin | 260/606.5 P |

OTHER PUBLICATIONS

Epstein et al., Tetrahedron Letters, v18, pp. 1231–1242, pp. 1211–1219 (1962).
Buckler, J.A.C.S., v82, pp. 4215–4220 (1960).
Buckler et al., J.A.C.S., v82, pp. 2076–2077 (1960).
Trippett, J. Chem. Soc. pp. 2813 2816 (1961).
Hellmann et al., Ann., v659, pp. 49–63 (1962).
Petrov et al., Russ. Chem. Rev., v37, pp. 437–439 (1968).
Kosolapoff et al., Organic Phosphorus Compounds, Wiley–Interscience, N.Y. vol. 1, pp. 99, 100 (1972).
Cotton Progress in Inorganic Chemistry, Interscience Publ., N.Y., vol. 5, pp. 47–49 (1963).

*Primary Examiner*—Helen M. S. Sneed
*Attorney, Agent, or Firm*—Connolly and Hutz

[57] ABSTRACT

Production of halogen-containing tertiary phosphine oxides of the general formula (I)

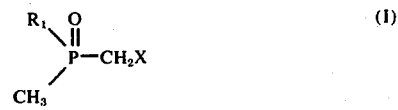

in which $R_1$ stands for an alkyl, halogenoalkyl, alkenyl, halogenoalkenyl, alkinyl or halogenoalkinyl radical, each of these radicals containing from 1 to 18 carbon atoms, or stands for a cycloalkyl, a halogenated cycloalkyl, an aryl, a halogenated aryl, an aralkyl or a halogenated aralkyl radical, and X stands for halogen.

The oxides are made by subjecting a compound of the general formula (II)

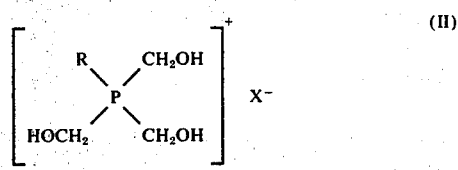

in which R has the same meaning as $R_1$ and X stands for halogen, to thermal treatment in the presence of hydrogen halide at atmospheric or at elevated pressure so as to split off water and formaldehyde in vapor form therefrom; by continuously freeing the resulting reaction mixture from the said components in vapor form; by terminating the reaction and thereafter stripping off the hydrogen halide from the reaction mixture by introducing an inert gas thereinto; and by purifying the remaining crude product by distillation or recrystallization.

13 Claims, No Drawings

PRODUCTION OF HALOGEN-CONTAINING TERTIARY PHOSPHINE OXIDES

The present invention relates to the production of halogen-containing tertiary phosphine oxides from quaternary phosphonium halides.

It has already been described (cf. K. A. PETROV, Z. H. Obshck, Khim. 35 2062 (1965)) that dibutyl-hydroxymethylphosphine oxide can be reacted with thionyl chloride in accordance with the following reaction equation

so as to obtain dibutyl-chloromethyl-phosphine oxide in a yield of 63.8 %. A disadvantage encountered in this reaction resides in the formation, per mol of phosphine oxide, of one mol of sulfur dioxide and of one mol of hydrogen chloride, which are corrosive agents and therefore have to be neutralized or disposed of.

A further process has been reported in German published Specification Offenlegungsschrift No. 2,060,217, wherein dialkyl-hydroxyalkyl-phosphine oxides are reacted with phosgene in accordance with the following reaction equation

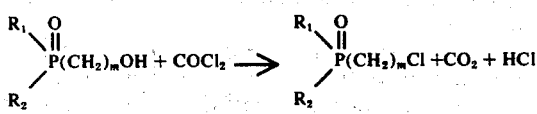

to produce the corresponding dialkyl-chloroalkyl-phosphine oxides.

Disadvantageous phenomena of this process reside in the use of very toxic phosgene and in the formation, per mol of phosphine oxide, of one mol of hydrogen chloride which has to be neutralized, expelled or disposed of.

A still further process for making tetrakis-(chloromethyl)phosphonium chloride has been described by A. Hoffmann in J. Amer. Chem. Soc. 52, page 2995 (1930), wherein tetrakis-(hydroxymethyl)-phosphonium chloride is reacted with PCl$_5$.

The present invention now provides a process which is free from the disadvantageous phenomena referred to hereinabove.

The process of the present invention for making halogencontaining tertiary phosphine oxides of the general formula I

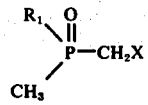

in which R$_1$ stands for an alkyl, halogenoalkyl, alkenyl, halogenoalkenyl, alkinyl or halogenoalkinyl radical, each of these radicals containing from 1 to 18 carbon atoms, or stands for a cycloalkyl, a halogenated cycloalkyl, an aryl, a halogenated aryl, an aralkyl or a halogenated aralkyl radical, and X stands for halogen, comprises subjecting a compound of the general formula II

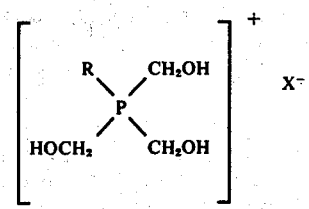

in which R stands for an alkyl, halogenoalkyl, alkenyl, halogenoalkenyl, alkinyl or halogenoalkinyl radical, each of these radicals containing from 1 to 18 carbon atoms, or stands for a cycloalkyl, a halogenated cycloalkyl, an aryl, a halogenated aryl, and aralkyl or a halogenated aralkyl or a —CH$_2$OH-radical and X stands for halogen, to thermal treatment in the presence of hydrogen halide at atmospheric or at elevated pressure so as to split off water and formaldehyde in vapor form therefrom; continuously freeing the resulting reaction mixture from the said components in vapor form; terminating the reaction and thereafter stripping off the hydrogen halide from the reaction mixture by introducing an inert gas thereinto; and purifying remaining crude product by distillation or recrystallization.

A preferred feature of the present process comprises making phosphine oxide derivatives of the general formula (I), in which the substituent R$_1$ stands for an alkyl, halogenoalkyl, alkenyl, halogenoalkenyl, alkinyl or halogenoalkinyl radical, each of these radicals having from 1 to 4 carbon atoms, or preferably stands for a methyl, —CH$_2$Cl or cyclohexyl radical, and X stands for chlorine or bromine.

A further preferred feature of the process of the present invention comprises thermally splitting off water and formaldehyde from the phosphonium salt at temperatures within the range about 130° and 250° C, at atmospheric pressure or under pressures up to about 20 atmospheres gauge. The hydrogen halide is used in a proportion understoichiometric with respect to the number of hydroxyl groups present in the starting material, and it should conveniently contain an anion corresponding to that being contained in the phosphonium salt of formula (II) which is used as the starting material.

A further preferred feature of the present process comprises splitting off water and formaldehyde from a melt or a solution of the starting material in an inert solvent forming an azeotrope with water. Suitable inert solvents are, for example: ortho-dichlorobenzene, xylene, p-chlorotoluene, trimethylbenzene, tetramethylbenzene, tetralin, decane or dodecane.

Reaction water originating from the splitting operation and formaldehyde should conveniently be removed continuously from the reaction mixture, in admixture with the solvent. After termination of the reaction, the reaction mixture should be further processed after having been freed from hydrogen halide, which may be retained therein. This may be done, for example, by flowing nitrogen, carbon dioxide or argon therethrough, at temperatures within the range about 100° and 250° C. The slightly acid crude final product freed substantially from hydrogen halide can be purified completely by first neutralizing it with a metal carbonate, such as Na$_2$CO$_3$, K$_2$CO$_3$ or CaCO$_3$ and then distilling or recrystallizing it.

The process of the present invention can more particularly be effected in the following manner, for example:

A phosphonium salt of general formula (II) is placed in a heatable reactor provided with a thermometer, a hydrogen halide inlet opening into the reactor down to its bottom and with an agitator, and heated therein to the reaction temperature, at atmospheric pressure.

The reactor is connected to a heatable column, which is operated at 110°–160° C, and to a condenser downstream thereof, for deaeration.

During the initial heating period, hydrogen halide should preferably be introduced into the salt so as to have an acid medium in the reaction mixture and to avoid undesirable decomposition reactions. Once the desirable reaction temperature has been reached, hydrogen halide is supplied per unit time in quantities which are completely absorbed by the reaction mixture. This is controlled by means of an off-gas meter, e.g. a bubble counter or rotameter, arranged downstream of the condenser.

At the same time, the resulting reaction water and the formaldehyde split off, which are substantially free from hydrogen halide, are continually distilled off and collected downstream of the condenser. Towards the end of the reaction, where the conversion is high, the quantity of hydrogen halide supplied per unit time at the onset of the reaction ceases to be completely absorbed. This is indicated by the passage of gas trough the off-gas meter. If the conversion fails to be complete at that moment, it is necessary for the supply of hydrogen halide per unit time to be so reduced that the off-gas meter indicates slight gas flow. In this case an aqueous solution of formaldehyde and hydrogen halide is obtained downstream of the condenser.

After termination of the reaction, it is possible for the reaction product having minor amounts of hydrogen halide dissolved or absorbed therein to be freed therefrom by stripping with an inert gas, e.g. nitrogen, carbon dioxide or argon at temperatures within the range 100° to 250° C, or to be neutralized by treating the melt with an alkali metal carbonate, e.g. Na$_2$CO$_3$, K$_2$CO$_3$ or CaCO$_3$. In this latter case, precipitated alkali metal halide is filtered off and water originating from the neutralization is removed under vacuum. The resulting crude reaction product containing phosphine oxide can be purified by distillation under vacuum, recrystallization or in another manner.

As reported above, it is possible for the present process to be carried out in the presence of an inert solvent. In this case, a solvent/water/formaldehyde mixture in vapor form is continuously removed from the reactor via the column placed downstream thereof. The column is operated at temperatures between 110° and 160° C. At those temperatures, it is possible for evaporating reaction product, if any, to be condensed and recycled to the reactor.

Under the operational conditions selected, the present process would have been expected to provide for a complete replacement of the hydroxy groups by halogen atoms which, however, is unexpectedly not the case. The products of the present invention are commercially interesting flame-proofing agents.

EXAMPLE 1

A 250 cc round flask placed in an oil bath and provided with a gas inlet opening thereinto down to its bottom, an efficient cooler and a thermometer was fed with 104.5 g or 0.6 mol of tris-(hydroxymethyl)-methylphosphonium chloride which was rapidly heated therein to 220° C. At about 180° C, gaseous hydrogen chloride was introduced in the quantity necessary to ensure complete absorption by the melt. Once the reaction temperature was at 220° C, the melt was supplied initially with 1 l/h of hydrogen chloride over a period of 15 minutes and then with 10–20 l/h. After about 30 minutes, the quantity of HCl, which was absorbed, dropped down to 5–10 l/h and the off-gas was found to have hydrogen chloride therein. The supply of hydrogen at a rate of 5 l/h was continued for a further 15 minutes to complete the reaction. Water originating from the reaction and the formaldehyde split off were expelled via a packed column heated to 120° C and condensed in a cooler. The condensate was an aqueous formalin solution in hydrochloric acid. A portion of the formaldehyde was found to have precipitated in solid form.

A sample of the reaction mixture was subjected to $^1$H-NMR spectroscopy which indicated an almost complete conversion of tris-(hydroxymethyl)-methylphosphonium chloride to chloromethyl-dimethyl-phosphine oxide.

Residual water or hydrogen chloride, if any, was expelled by flowing nitrogen over 30 minutes at 220° C through the crude product, which then contained less than 2 % of these two substances.

36 g of a mixture of aqueous and solid condensate was obtained, containing 20 weight % of HCl and 17.8 g of formaldehyde. Crude product containing 1.8 weight % of HCl was obtained in a yield of 74 g (97.5 % of the theoretical).

To purify the crude product completely, it was admixed at 100°–110° C with agitation with a quantity of finely pulverized sodium carbonate, which was equivalent to the quantity of HCl therein. After 15 minutes, it was filtered off while hot from the precipitated HCl. Following this, the water of neutralization was distilled off under the vacuum of a water jet pump and the residue was distilled off at 132°–133° C at 17 mm Hg.

69.6 g of colorless crystalline chloromethyl-dimethyl-phosphine oxide was obtained in a yield of 91.6 % of the theoretical. The salt residue was extracted with methylene chloride and a further 1.2 g of chloromethyl-dimethylphosphine oxide was recovered therefrom. The total yield was 93.2 % of the theoretical. $^1$H-NMR-spectroscopy indicated that the product had a purity of 97.2 %. Gas chromatography indicated a purity of 97.8 %. The melting point was between 72° and 75° C. The product as contaminated with minor amounts of trimethyl-phosphine oxide and bis-(chloromethyl)-methylphosphine oxide.

EXAMPLE 2

87.2 g (0.5 mol) of tris-(hydroxymethyl)-methylphosphonium chloride was placed in an acidproof autoclave with stirrer and heated therein to 180°–185° C. Hydrogen chloride was introduced until a pressure of 3.6 atmospheres gauge was found to have been established in the interior of the autoclave. After a short time, the pressure dropped slightly. A further quantity of hydrogen chloride was supplied (8 g) whereby the pressure increased to 4 atmospheres gauge. After 2.5 hours, hydrogen chloride was supplied once again so that the pressure increased to 8 atmospheres gauge. Under that pressure and at 190° C, the reaction mixture was stirred for 1 hour, cooled with relief of pressure, and the material in the autoclave was scavenged with nitrogen. Following this, the reaction product was subjected to fractional distillation under a vacuum of 15 mm Hg. 53.7 g of chloromethyl-dimethylphosphine oxide ($bp_{15}$ = 128°–130° C) was obtained. This corresponded to a yield of 84.8 % of the theoretical.

EXAMPLE 3

A mixture of 104.5 g (0.6 mol) of tris-(hydroxymethyl)methyl-phosphonium chloride and 300 cc of ortho-dichlorobenzene was heated to boiling under reflux. The whole was stirred vigorously and hydrogen chloride was introduced thereinto. After about 16 hours, the reaction water (11.7 cc) and the bulk of formaldehyde split off were expelled together with the solvent. The reaction product was subjected to fractional distillation under vacuum at 116°–120° C at 12 mm Hg and 57.6 g of chloromethyl-dimethylphosphine oxide was obtained in a yield of 76 % of the theoretical.

EXAMPLE 4

102 g (0.42 mol) of tris-(hydroxymethyl)-cyclohexylphosphonium chloride was melted in the reactor described in Example 1. During the initial heating period, 2-3 l of gaseous hydrogen chloride was introduced thereinto within 15 minutes. The quantity of gas supplied was reduced down to 1-2 l/h as soon as the off-gas was found to contain hydrogen chloride. The reaction was completed by heating the whole for a further 20 minutes to 215°–220° C. The reaction water and the formaldehyde split off were expelled in the manner described in Example 1 and condensed. 25 g of a condensate containing 12 g of formaldehyde and 5.5 g of HCl was obtained.

The crude product was freed from hydrogen chloride dissolved therein by flowing nitrogen therethrough over 30 minutes at about 200° C and then distilled at 135°–136° C under a vacuum of 0.3 mm Hg. 67 g of colorless chloromethyl-cyclohexyl-methyl phosphine oxide melting at 51°–53° C was obtained. This corresponded to a yield of 82 % of the theoretical. NMR-analysis ($^{31}$P-NMR: - 50 ppm) indicated that the product had a purity of 99.5 %.

We claim:

1. A process for making halogen-containing tertiary phosphine oxides of the general formula (I)

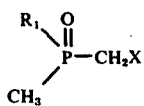

(I)

in which $R_1$ is selected from the group consisting of alkyl, halogenoalkyl, alkenyl, halogenoalkenyl, alkinyl and halogenoalkinyl containing from 1 to 18 carbon atoms, cycloalkyl, halogenated cycloalkyl, aryl, halogenated aryl, aralkyl and halogenated aralkyl, and X is halogen, which process comprises subjecting a compound of the general formula (II)

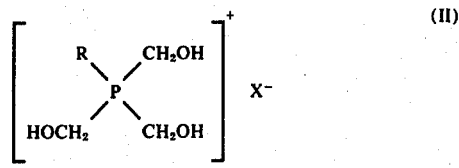

(II)

in which R is selected from the group consisting of alkyl, halogenoalkyl, alkenyl, halogenoalkenyl, alkinyl and halogenoalkinyl containing from 1 to 18 carbon atoms, cycloalkyl, halogenated cycloalkyl, aryl, halogenated aryl, aralkyl halogenated aralkyl and —CH$_2$OH—, and X is halogen, to thermal treatment in the presence of hydrogen halide at atmospheric or at elevated pressure so as to split off water and formaldehyde in vapor form therefrom; continuously freeing the resulting reaction mixture from the said components in vapor form; terminating the reaction and thereafter stripping off the hydrogen halide from the reaction mixture by introducing an inert gas thereinto; and purifying the remaining crude product by distillation or recrystallization.

2. The process as claimed in claim 1, wherein $R_1$ is alkyl, halogenoalkyl, alkenyl, halogenoalkenyl, alkinyl or halogenoalkinyl each having from 1 to 4 carbon atoms.

3. The process as claimed in claim 1, wherein $R_1$ is methyl, cyclohexyl or —CH$_2$Cl.

4. The process as claimed in claim 1, wherein X is chlorine or bromine.

5. The process as claimed in claim 1, wherein the anion of the hydrogen halide corresponds to the anion of the phosphonium salt of formula (II).

6. The process as claimed in claim 1, wherein the water and formaldehyde are split off thermally at temperatures within the range about 130° to 250° C.

7. The process as claimed in claim 1, wherein the water and formaldehyde are split off thermally under a pressure of up to about 20 atmospheres gauge.

8. The process as claimed in claim 1, wherein the water and formaldehyde are split off thermally in the presence of a quantity of hydrogen halide being understoichiometric with respect to the number of hydroxyl groups contained in the starting material.

9. The process as claimed in claim 1, wherein water and formaldehyde are split off from a melt or a solution of the starting material in an inert solvent forming an azeotrope with water.

10. The process as claimed in claim 9, wherein the inert solvent is selected from the group consisting of ortho-dichlorobenzene, xylene, p-chlorotoluene, trimethylbenzene, tetramethylbenzene, tetralin, decalin, decane and dodecane.

11. The process as claimed in claim 9, wherein the reaction water and formaldehyde are continually removed from the reaction mixture in admixture with the inert solvent.

12. The process as claimed in claim 1, wherein the hydrogen halide is expelled from the reaction mixture by flowing nitrogen, carbon dioxide or argon therethrough at temperatures within the range about 100° to 250° C.

13. The process as claimed in claim 1, wherein the acidic crude product is neutralized with Na$_2$CO$_3$, K$_2$CO$_3$ or CaCO$_3$ and then neutralized.

* * * * *